(12) United States Patent
Luks et al.

(10) Patent No.: US 6,368,322 B1
(45) Date of Patent: Apr. 9, 2002

(54) SURGICAL BONE SCREW

(75) Inventors: Howard J. Luks, Ossining, NY (US); John W. Boyle, Upper Montclair, NJ (US); Lawrence A. Shimp, Morganville, NJ (US); David R. Kaes, Toms River, NJ (US); John W. Morris, Beachwood, NJ (US); Erik O. Martz, Jackson, NJ (US); Daniel E. Rosenthal, Milburn, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/542,556

(22) Filed: Apr. 3, 2000

Related U.S. Application Data

(60) Provisional application No. 60/127,560, filed on Apr. 2, 1999.

(51) Int. Cl.[7] .................................................. A61B 17/86
(52) U.S. Cl. ........................................................ 606/73
(58) Field of Search ............................. 606/72, 73, 76; 623/13.11, 13.12, 13.14, 13.17, 23.63, 925; 411/402, 403, 410

(56) References Cited

U.S. PATENT DOCUMENTS

| | | | |
|---|---|---|---|
| 3,739,773 A | | 6/1973 | Schmitt et al. |
| 4,877,020 A | * | 10/1989 | Vich |
| 4,924,865 A | | 5/1990 | Bays et al. |
| 4,950,270 A | | 8/1990 | Bowman et al. |
| 4,976,715 A | | 12/1990 | Bays et al. |
| 5,053,036 A | | 10/1991 | Perren et al. |
| 5,084,050 A | | 1/1992 | Draenert |
| 5,129,906 A | | 7/1992 | Ross et al. |
| 5,169,400 A | | 12/1992 | Mühling et al. |
| 5,364,400 A | | 11/1994 | Rego, Jr. et al. |
| 5,439,684 A | | 8/1995 | Prewett et al. |
| 5,443,509 A | | 8/1995 | Boucher et al. |
| 5,470,334 A | | 11/1995 | Ross et al. |
| 5,584,836 A | | 12/1996 | Ballintyn et al. |
| 5,792,142 A | | 8/1998 | Galitzer |
| 5,827,287 A | | 10/1998 | Tunc |
| 5,868,749 A | | 2/1999 | Reed |
| 5,904,685 A | * | 5/1999 | Walawalker .................. 606/73 |
| 5,968,047 A | | 10/1999 | Reed |
| 6,045,554 A | * | 4/2000 | Grooms ........................ 606/73 |
| 6,099,529 A | * | 8/2000 | Gertzman et al. ............. 606/73 |

FOREIGN PATENT DOCUMENTS

| | | |
|---|---|---|
| EP | 471334 A1 | 2/1992 |
| EP | 0615732 | 2/1994 |
| GB | 2175807 | 10/1991 |

OTHER PUBLICATIONS

Obwegeser, Joachim A., Bioconvertible screws made of allogenic cortical bone for osteosynthesis following sagittal split ramus osteotomy without postoperative immobilisation, Journal of Cranio–Maxillo–Facial Surgery (1994) 22. 63–75.

Albee, Fred H.Albee, M.D., LL.D, Sc.D., F.A.C.S., F.I.C.S., Bone Graft Surgery in Disease, Injury and Deformity, D. Appleton–Century Company.

Albee, Fred H., M.D., F.A.C.S., The Improved Albee Bone Mill, article, D. Appleton–Century Company, Inc., 1940.

* cited by examiner

*Primary Examiner*—Jeffrey A. Smith
(74) *Attorney, Agent, or Firm*—Dilworth & Barrese, LLP

(57) ABSTRACT

An interference screw suitable for surgical use is provided. The interference screw is constructed from bone and includes an elongated body having an outer threaded surface, a tapered insertion end and a central throughbore. Insertion tool engaging structure is formed along the walls defining the throughbore. The insertion tool engaging structure extends from the proximal end of the elongated body over a substantial portion of the length of the elongated body. The insertion tool engaging structure functions to distribute the forces required to insert the interference screw throughout the body of the interference screw to prevent fracturing of the interference screw during insertion into bone.

16 Claims, 5 Drawing Sheets

SURGICAL BONE SCREW

CROSS REFERENCE TO RELATED APPLICATIONS

This application claims priority from U.S. provisional application Ser. No. 60/127,560, filed Apr. 4, 1999 which is incorporated herein by reference.

BACKGROUND OF THE INVENTION

1. Technical Field

The present disclosure relates generally to surgical interference screws and, more particularly, to surgical interference screws constructed from bone and adapted to compress soft tissue, e.g., ligaments, tendons, etc., against bone in a bone tunnel.

2. Background of Related Art

Surgical interference screws for attaching soft tissue, such as ligaments and tendons, to bone are well known. Typically, because of the relatively large amount of torque that must be applied to an interference screw during insertion, these screws are constructed from metal. The use of metal screws, however, sometimes necessitates surgical procedures for screw removal. Moreover, metal screws have a tendency to loosen and/or back out of a previously formed bore and result in bone loss.

Interference screws have also been constructed from bioabsorbable polymers, e.g., polyglycolic acid polymers. The degradation time of such polymers is selected to coincide with the healing time of the tissue being repaired. Typically, after degrading, bioabsorbable polymers leave acetic acid deposits which may lead to bone degradation and inflammatory reactions in the adjacent tissue.

Another problem associated with using interference screws formed from a bioabsorbable material is that the bioabsorbable material is likely to have a significantly lower strength and cannot be subjected to the high torque required for insertion. The distal region of a bioabsorbable screw is particularly susceptible to shear failure due to excess torque.

Screws made of human or animal bone are also known. For example, U.S. Pat. Nos. 5,968,047 and 5,868,749 issued to Thomas M. Reed disclose screws made from cortical and cancellous bone. Reed's bone screws include a head portion configured to engage a driver. The head portion, for example, may include a hexagonal recess, a cruciform recess or philips recess to receive a drive tool. One problem associated with screws made of bone is that bone has a tendency to split or fracture at the interface with the driver tool. This problem is aggravated when using a driver that exerts expansion forces on the screw, such as a driver for engaging a screw having a hexagonal recess or a philips head.

Accordingly, a need exists for an improved surgical screw which can remain in the body after insertion, does not adversely effect adjacent tissue and has the requisite strength characteristics to be inserted into bone without fracturing. Moreover, a need exists for an insertion tool for inserting bone screws which stabilizes the screw at the screw/tool interface to prevent fracture of the screw during screw insertion.

SUMMARY

In accordance with the present disclosure, an interference screw for surgical use is provided which is formed from bone, such as the ridge of the tibia. The interference screw includes an elongated body having a proximal end adapted to engage a screw insertion tool and a distal insertion end. The insertion end is tapered to facilitate entry into a bone tunnel formed in the bone. A bore extends through at least a portion of the elongated body. Insertion tool engaging structure is formed along at least a portion of the bore. The insertion tool engaging structure extends within the bore along a substantial portion of the length of the elongated body. In one embodiment of the presently disclosed interference screw, the proximal end of the interference screw includes a hexagonal head portion and the insertion tool engaging structure includes hexagonal walls defining the bore. The hexagonal walls extend from the proximal end of the elongated body distally to the point at which the tapered insertion end of the elongated body begins to taper. The outer surface of the elongated body also includes a helical thread which extends from the head portion to the distal end of the elongated body.

In another preferred embodiment of the interference screw, the elongated body includes a helical thread that extends from the proximal to the distal end of the elongated body. The insertion tool engaging structure also includes hexagonal walls defining the bore. The hexagonal walls extend over a substantial portion of the length of the elongated body and are configured to engage an insertion tool. In yet another preferred embodiment, a slot is formed in the elongated body through the hexagonal walls. The slot and the hexagonal walls extend from the proximal end of the elongated body to the point at which the insertion end of the elongated body begins to taper.

The interference screw is suitable for surgical use and may be used to secure soft tissue against bone. Typically, during an ACL reconstruction procedure, a bone-patellar tendon-bone graft (BPTB) is taken from the central ⅓ of the patient's patellar tendon. Therefore, the reconstructed ACL is actually part of the patellar tendon with two blocks of bone on either end, from the patella and the tibial tuberacle. One of these blocks of bone is actually what gets placed inside the bone tunnel and fixed in place with an interference screw. The soft-tissue structure is intimately and biologically attached to the bone block, but it is actually the block of bone that gets compressed inside the tunnel. However, interference screws can also be used to wedge tendons against bone. Such a procedure would include an anterior cruciate ligament (ACL) reconstruction procedure. Interference screws are also used to attach bone against bone, not (Oust) soft tissue against bone. By constructing the screw from bone, several advantages are achieved. For example, bone resorbs by biological remodeling, not by chemical means. As such, bone is replaced by bone as it resorbs. Thus, the loss of strength during the resorption phase is less and more predictable than with a resorbable polymer. Moreover, bone bonds to bone. The fixation of the interference screw is enhanced as bone grows directly on to the surface of the interference screw.

Fixation of the interference screw is enhanced by a biological bond, while metal and polymer screws must depend only on a mechanical interlock with bone.

BRIEF DESCRIPTION OF THE DRAWINGS

Various preferred embodiments of the surgical interference screw are described herein with reference to the drawings, wherein.

DETAILED DESCRIPTION OF PREFERRED EMBODIMENTS

Figure 1:
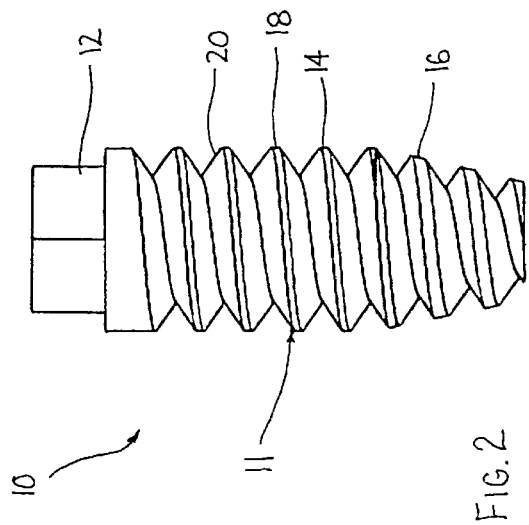
FIG. 1 is a perspective view of one embodiment of the presently disclosed surgical interference screw.
Figure 2:
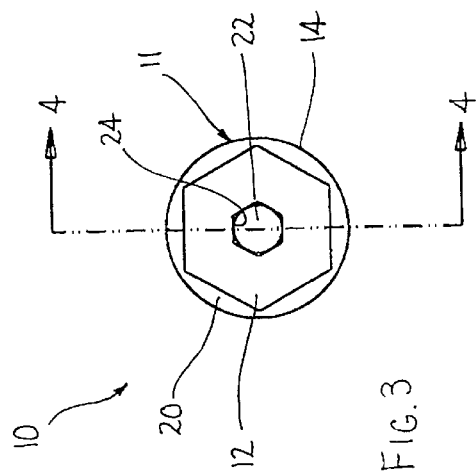
FIG. 2 is a side view of the surgical interference screw shown in FIG. 1.
Figure 3:
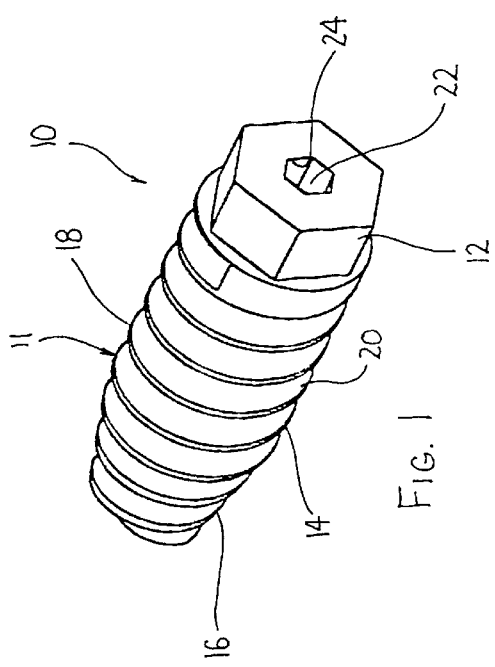
FIG. 3 is a top view of the surgical interference screw shown in FIG. 1.
Figure 4:
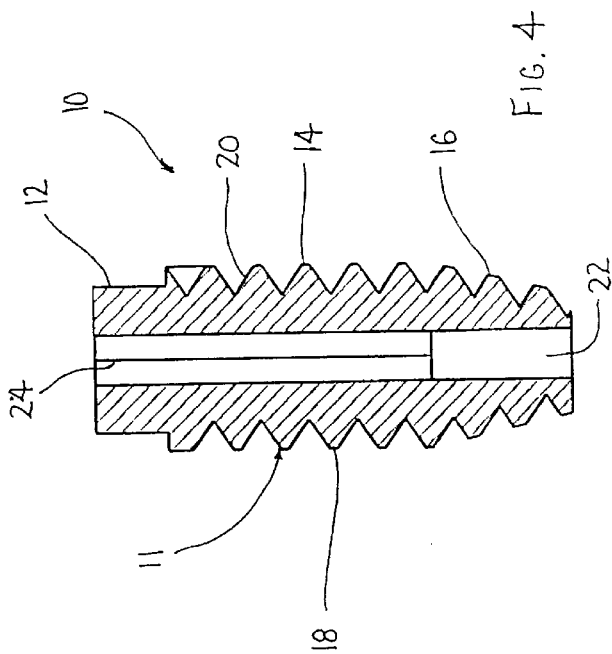
FIG. 4 is a cross-sectional view of the surgical interference screw taken along section line 4—4 of FIG. 3.
Figure 6:
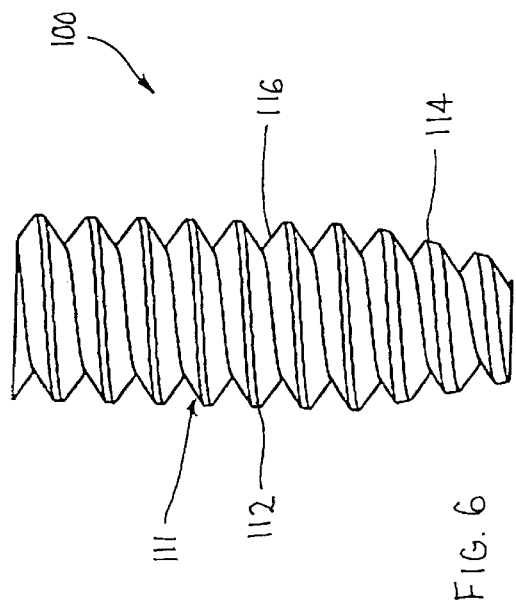
FIG. 6 is a side view of the surgical interference screw shown in FIG. 5.
Figure 7:
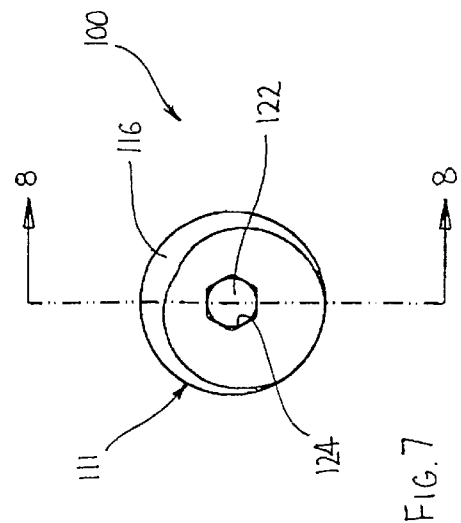
FIG. 7 is a top view of the surgical interference screw shown in FIG. 5.
Figure 5:
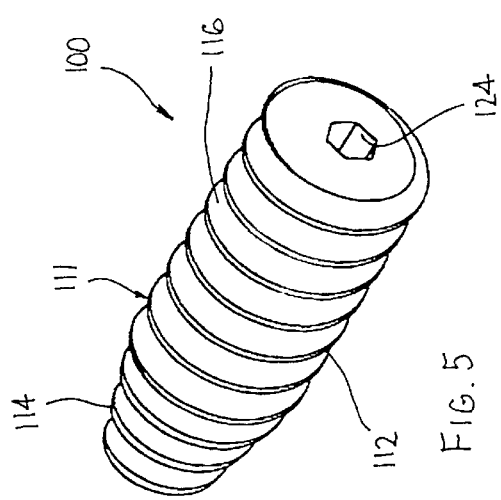
FIG. 5 is a perspective view of another embodiment of the presently disclosed surgical interference screw.
Figure 8:
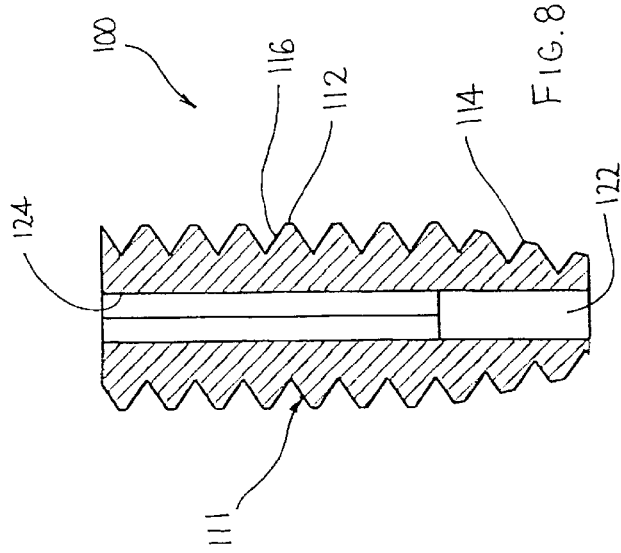
FIG. 8 is a cross-sectional view of the surgical interference screw taken 15 along section line 8—8 of FIG. 7.
Figure 10:
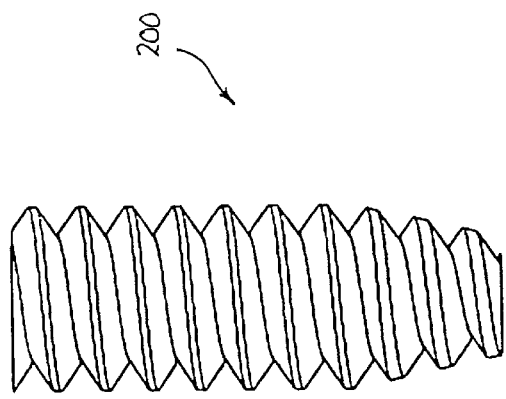
FIG. 10 is a side view of the surgical interference screw shown in FIG. 9.
Figure 11:
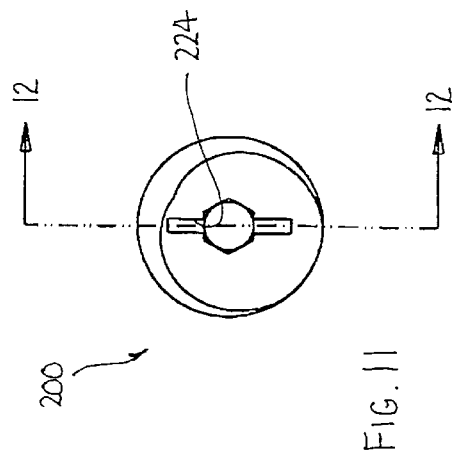
FIG. 11 is a top view of the surgical interference screw shown in FIG. 9.
Figure 9:
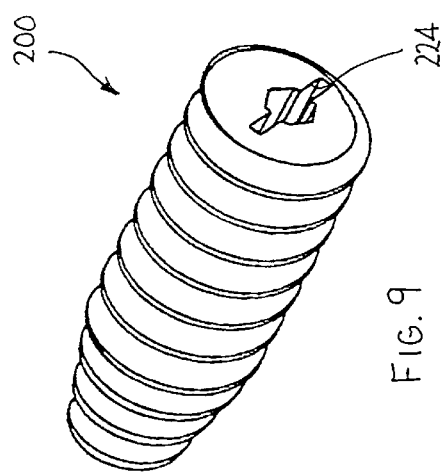
FIG. 9 is a perspective view of yet another embodiment of the presently disclosed surgical interference screw.
Figure 12:
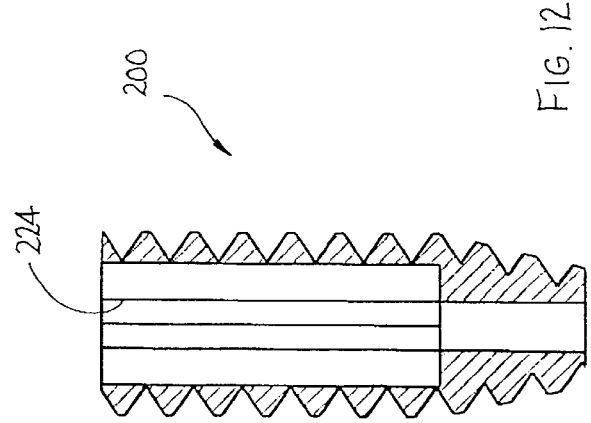
FIG. 12 is a cross-sectional view of the surgical interference screw taken along section line 12—12 of FIG. 11.

Preferred embodiments of the presently disclosed bone screw and insertion tool will now be described in detail with reference to the drawings, in which like reference numerals designate identical or corresponding elements in each of the several views.

FIGS. 1–4 illustrate one preferred embodiment of the presently disclosed interference screw, shown generally as 10. Briefly, interference screw 10 includes a body 11 having a hexagonal head portion 12 and a threaded body portion 14. Body portion 14 includes a distally tapered insertion end 16 and a substantially cylindrical central body portion 18. A helical thread 20 extends from central body portion 18 to the distal end of insertion end 16.

A central bore 22 extends through hexagonal head 12 and threaded body portion 14. At least a portion of central bore 22 is formed with insertion tool engaging structure which includes hexagonally-shaped walls 24. The walls 24 are configured to receive an insertion tool (not shown) for inserting the insertion screw into bone during a surgical procedure. Hexagonally-shaped walls 24 function to distribute the torque applied to interference screw 10 throughout body 11 to prevent shearing of the screw during insertion. Hexagonally-shaped walls 24 of central bore 22 extend along a substantial portion of the length of the central bore 22, and preferably extend throughout central body portion 18 to a point at which the insertion end 16 of elongated body 11 begins to taper. Although illustrated as being hexagonally-shaped, it is also envisioned that walls 24 may define other configurations suitable for distributing the insertion forces throughout the body of the interference screw, e.g., square, triangular, etc.

Interference screw 10 is constructed from bone having a cortical thickness sufficient to satisfy the requisite strength requirements for insertion. For example, interference screw 10 may be produced from the ridge of the tibia such as by coring the bone using a drill press and thereafter machining and tapping the body 11 to form head portion 12 and threaded body portion 14. Alternately, interference screw 10 may be formed from bone particles such as disclosed in U.S. patent application Ser. No. 09/256,447, now U.S. Pat. No. 6,294,187, entitled "Load-Bearing Osteoimplant, Method For Its Manufacture And Method Of Repairing Bone Using Same", which is hereby incorporated by reference. Interference screw 10 is preferably 8–12 mm in outer diameter and 10–35 mm in length, although the size of the interference screw 10 would depend on the particular surgical use and accordingly may vary from that discussed above.

FIGS. 5–8 illustrate another embodiment of the presently disclosed interference screw, shown generally as 100. Interference screw 100 is similar in all respects to screw 10 except that interference screw 100 does not include a hexagonal head. Interference screw 100 includes a body 111 having a central body portion 112 and a distally tapered insertion end portion 114. Body 111 has a helical thread 116 that extends about central body portion 112 and insertion end portion 114. A central bore 122 extends through body 111 and includes insertion tool engaging structure 124 which extends over a substantial portion of the length of central bore 122. Insertion tool engaging structure 124, although illustrated as being hexagonal may assume any shape capable of distributing the insertion force of the insertion tool (not shown) throughout body 111. As discussed above, insertion tool engaging structure 124 preferably extends distally through central body portion 112 to a point at which the insertion end 114 of elongated body 111 begins to taper.

FIGS. 9–12 illustrate another embodiment of the presently disclosed bone screw, shown generally as 200. Bone screw 200 is similar to bone screw 100 in all respects except that insertion tool engaging structure 224 has a slotted hexagonal shape. Slotted hexagonal insertion tool engaging structure 224, as discussed above, distributes the forces required to insert the bone screw into bone throughout the bone screw to prevent screw fracture.

Each of the interference screws disclosed above can be used to compress soft tissue, e.g., tendons or ligaments, against bone. For example, the above-described interference screws can be used during an (ACL) reconstruction procedure. Typically, during an ACL reconstruction procedure, a bone-patellar tendon-bone graft (BPTB) is taken from the central ⅓ of the patient's patellar tendon. Therefore, the reconstructed ACL is actually part of the patellar tendon with two blocks of bone on either end, from the patella and the tibial tuberacle. One of these blocks of bone is actually what gets placed inside the bone tunnel and fixed in place with an interference screw. The soft-tissue structure is intimately and biologically attached to the bone block, but it is actually the block of bone that gets compressed inside the tunnel. However, interference screws can also be used to wedge tendons against bone. Interference screws are also used to attach bone against bone, not Oust) soft tissue against bone.

Figures 13, 14:
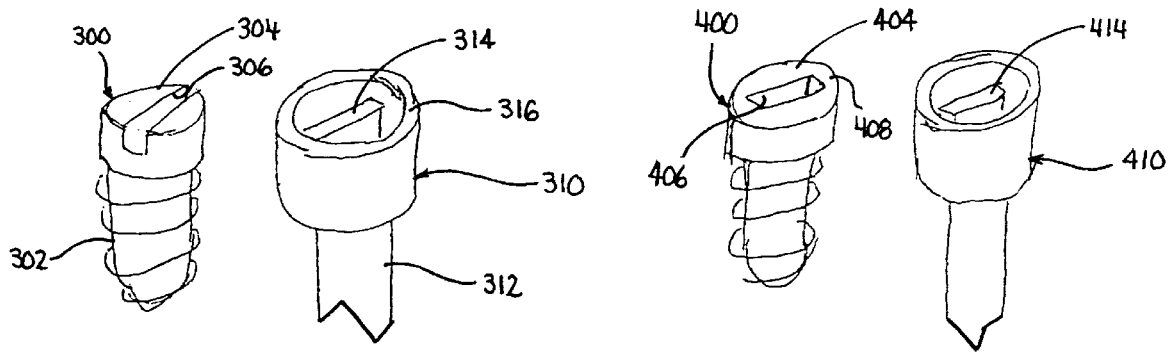
FIG. 13 is a perspective view of another embodiment of the presently disclosed bone screw having a rectangular slot in combination with an insertion tool.
FIG. 14 is a perspective view of another embodiment of the presently disclosed bone screw having a rectangular slot in combination with an insertion tool.

FIGS. 13–18 illustrate alternate embodiments of the presently disclosed bone screw in combination with an insertion tool. In FIG. 13, bone screw 300 includes a threaded body portion 302 and a head portion 304. Head portion 304 includes a rectangular slot 306. Insertion tool 310 includes an elongated body 312, an engaging member 314 and a restraining ring 316. Elongated body 312 includes a handle (not shown) to be grasped by a surgeon. Engaging member 314 is configured to be received within slot 306 in screw head portion 304. Restraining ring 316 is configured and dimensioned to fit snugly about head portion 304 of bone screw 300 during screw insertion. The inside diameter of restraining ring 316 should be approximately equal to the outside diameter of head portion 304.

Figures 15, 16:
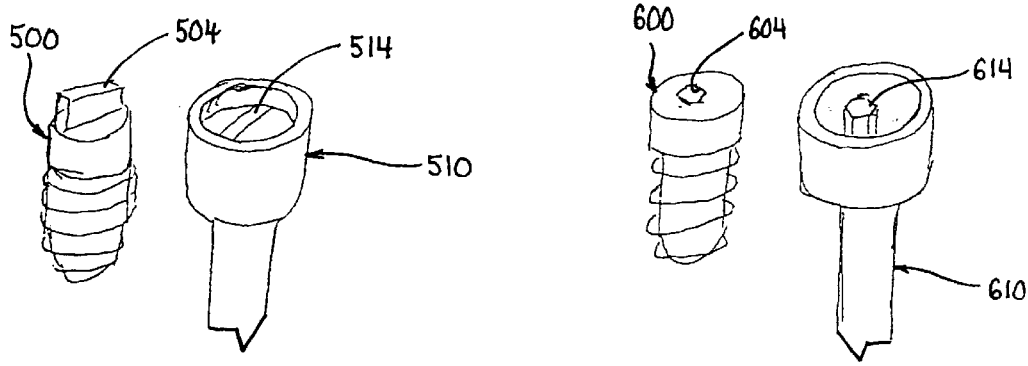
FIG. 15 is a perspective view of another embodiment of the presently disclosed bone screw having a rectangular projection in combination with an insertion tool.
FIG. 16 is a perspective view of another embodiment of the presently disclosed bone screw having a hexagonal bore in combination with an insertion tool.
Figure 17:
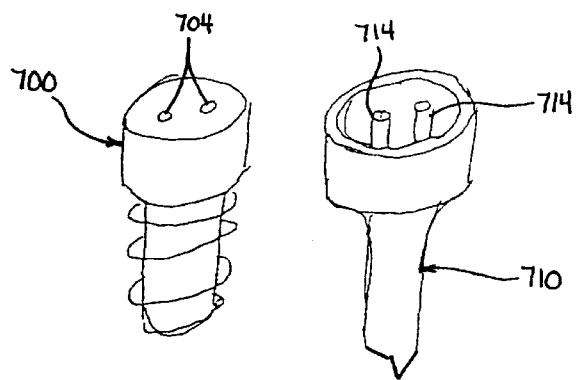
FIG. 17 is a perspective view of another embodiment of the presently disclosed bone screw having a pair of spaced cylindrical bores in combination with an insertion tool.

FIGS. 14–17 illustrate bone screw and insertion tool sets having a variety of configurations. In FIG. 14, screw 400 has a rectangular slot 406 formed in head portion 404 configured to receive engaging member 414 of insertion tool 410. Slot 406 does not extend through sidewall 408 of head portion 404. In FIG. 15, screw 500 includes a rectangular projection 504 configured to be received within rectangular slot 514 of insertion tool 510. In FIG. 16, screw 600 includes a hexagonal bore 604 configured to receive hexagonal projection 614 of insertion tool 610. In FIG. 17, screw 700 includes a pair of spaced cylindrical bores 704 configured to receive cylindrical projections 714 of insertion tool 710. Each of the above insertion tools includes a restraining ring configured and dimensioned to be received about the screw L head portion to provide stability to the screw head portion during screw insertion.

Figure 18:
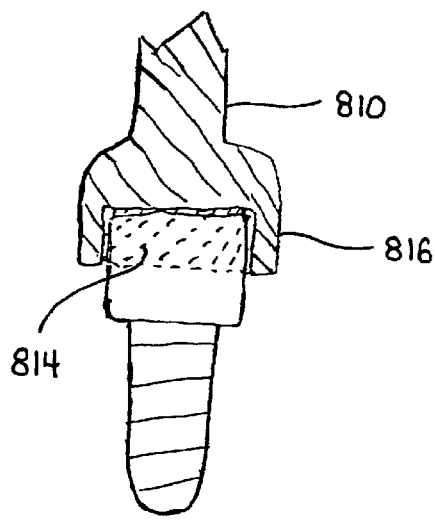
FIG. 18 is a side partial cross-sectional view of the bone screw and insertion tool shown in FIG. 13 with the insertion tool engaging the bone screw.
Figure 19:
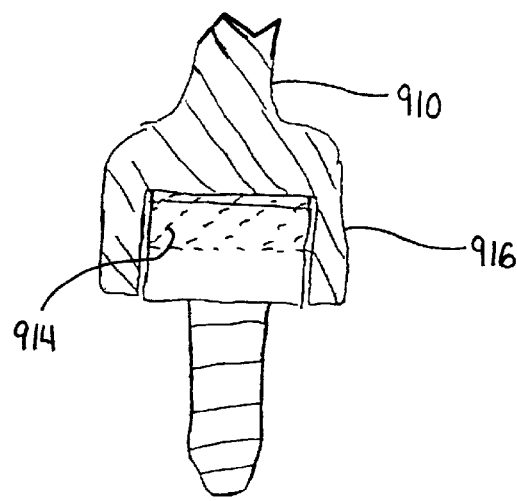
FIG. 19 is a side partial cross-sectional view of another embodiment of the presently disclosed bone screw and insertion tool with the insertion tool engaging the bone screw.
Figure 20:
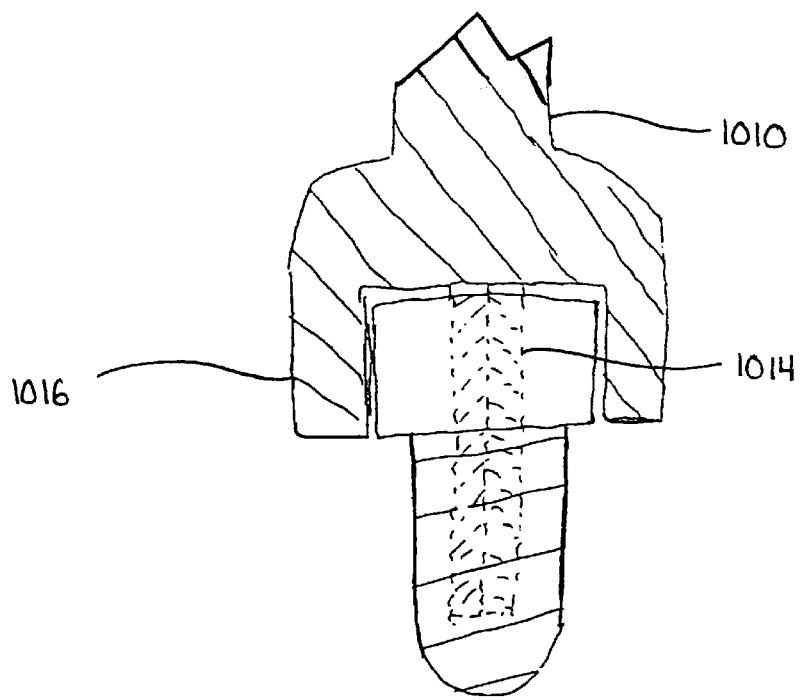
FIG. 20 is a side partial cross-sectional view of another embodiment of the bone screw and insertion tool shown in FIG. 16 with the insertion tool engaging the bone screw.

Referring to FIGS. 18–20, the dimension of the restraining ring in relation to the tool engaging member and the screw head portion may vary. For example, the depth of the recess formed by restraining ring 816 of insertion tool 810 is approximately equal to the height of engaging member 814 (FIG. 18). Alternately, the depth of the recess formed by restraining ring 916 can be greater than the height of engaging member 914 of insertion tool 910, or engaging member 1014 can have a height greater than the depth of the recess defined by the restraining ring 1016 (FIG. 20). With respect to elongated engaging member 1014, the relatively large driving surface area serves to distribute, and thus limit, breaking forces on the bone screw during screw insertion.

It will be understood that various modifications may be made to the embodiments disclosed herein. For example, the particular configuration of the insertion tool engaging structure defining the central bore need not be as illustrated but rather may assume any configuration capable of distributing the insertion forces throughout the body of the interference screw. Moreover, the insertion tool engaging structure may extend over the entire length of the central bore and need not end at the point that the insertion end begins to taper. Also, the shape of the insertion tool restraining ring may be varied to receive any shape bone screw head portion. Therefore, the above description should not be construed as limiting, but merely as exemplifications of preferred embodiments. Those skilled in the art will envision other modifications within the scope and spirit of the claims appended hereto.

What is claimed is:

1. A surgical interference screw for use in attaching bone to bone and soft tissue to bone, the interference screw comprising:
an elongated body having a proximal head portion and a distal insertion end and being constructed from bone, the elongated body defining a longitudinally extending bore which extends from the proximal head portion towards the distal insertion end, the longitudinally extending bore including engaging structure formed along at least a portion of the longitudinally extending bore, the engaging structure being configured and dimensioned to non-rotatably engage an insertion tool for inserting the interference screw into bone, and the proximal head portion being configured to simultaneously non-rotatably engage the iron tool to evenly distribute forces required to insert the interference screw throughout the interference screw during insertion of the interference screw into bone.

2. A surgical interference screw according to claim 1, wherein the distal insertion end is tapered.

3. A surgical interference screw according to claim 2, wherein the engaging structure extends from the proximal end of the elongated body to a position adjacent the distal insertion end.

4. A surgical interference screw according to claim 1, wherein the elongated body is threaded over at least a portion of its length.

5. A surgical interference screw according to claim 4, wherein the distal insertion end is tapered.

6. A surgical interference screw according to claim 5, wherein the proximal end of the elongated body includes a hexagonally-shaped head.

7. A surgical interference screw according to claim 6, wherein the engaging structure includes hexagonal-shaped walls defining the longitudinally extending bore.

8. A surgical interference screw according to claim 7, wherein the engaging structure extends along a substantial portion of the length of the elongated body.

9. A surgical interference screw comprising:
an elongated body including a head portion, a threaded body portion and a tapered insertion end, the head portion having an outer surface configured to non-rotatably engage an insertion tools and the elongated body defined an elongated bore confined to simultaneously non-rotatably engage the insertion tool to evenly distribute forces required to insert the interference screw throughout the interference screw during insertion of the interface screw into bone.

10. A surgical interference screw according to claim 9, wherein the elongated bore includes hexagonally-shaped walls.

11. A surgical interference screw according to claim 9, wherein the head portion is hexagonally shaped.

12. A surgical interference screw according to claim 9, wherein the elongated bore extends through a substantial portion of the length of the elongated body.

13. A surgical interference screw according to claim 9, wherein the width of the head portion is smaller than the diameter of the threaded body portion.

14. A surgical interference screw according to claim 9, wherein the elongated body is constructed from bone.

15. A surgical interference screw according to claim 9, wherein the bore and the head portion are hexagonally shaped.

16. A surgical interference screw according to claim 9, wherein the elongated body is constructed from bone.

* * * * *